(12) United States Patent
Osendowski

(10) Patent No.: US 6,802,853 B1
(45) Date of Patent: Oct. 12, 2004

(54) HAND HELD LASER DEVICE FOR STIMULATING HAIR GROWTH

(76) Inventor: Donald J. Osendowski, 2017 Ramona Rd., Waukesha, WI (US) 53186

(*) Notice: Subject to any disclaimer, the term of this patent is extended or adjusted under 35 U.S.C. 154(b) by 0 days.

(21) Appl. No.: 10/426,278

(22) Filed: Apr. 29, 2003

(51) Int. Cl.$^7$ ................................................. A61N 5/67
(52) U.S. Cl. ................................. 607/89; 606/9; 607/88
(58) Field of Search ........................... 607/88–94; 606/9

(56) References Cited

U.S. PATENT DOCUMENTS

| | | | |
|---|---|---|---|
| 6,283,956 B1 | * | 9/2001 | McDaniel .................... 606/9 |
| 6,497,719 B2 | | 12/2002 | Pearl et al. .................. 607/89 |
| 2002/0188334 A1 | * | 12/2002 | Carlgren ...................... 607/88 |
| 2003/0023283 A1 | * | 1/2003 | McDaniel ..................... 607/88 |

FOREIGN PATENT DOCUMENTS

| | | | | |
|---|---|---|---|---|
| GB | 0159446 A2 | * | 10/1985 | ........... A61H/39/00 |
| JP | 403228708 A | * | 10/1991 | ........... A46B/15/00 |
| JP | 407016304 A | * | 1/1995 | ............. A61N/5/06 |
| JP | 2001046527 A | * | 2/2001 | ............. A61N/5/06 |
| KR | 2002012969 A | * | 2/2002 | .......... A61H/23/02 |

* cited by examiner

*Primary Examiner*—Linda C. M. Dvorak
*Assistant Examiner*—Henry M Johnson, III
(74) *Attorney, Agent, or Firm*—Donald J. Ersler

(57) ABSTRACT

A laser device preferably includes a laser device body, at least one laser unit and at least one light emitting diodes (LED). The laser device body includes a cover which is attached to a top of a skirt. The skirt includes a contact skirt extending outward from a periphery of a mounting plate. The at least one laser unit and at least one LED are retained in the mounting plate. A DC power supply is preferably used to power the at least one laser unit and the at least one LED. A plurality of rounded projections extend from a bottom of the contact skirt. A strap is preferably included, such that the laser device may be retained by a hand of a user.

17 Claims, 3 Drawing Sheets

US 6,802,853 B1

HAND HELD LASER DEVICE FOR STIMULATING HAIR GROWTH

BACKGROUND OF THE INVENTION

1. Field of the Invention

The present invention relates generally to stimulating hair growth with lasers and more specifically to a hand held laser device for stimulating hair growth.

2. Discussion of the Prior Art

It appears that only one patent exists for a hand held device, which is capable of treating the scalp with a laser to stimulate hair growth. U.S. Pat. No. 6,497,719 to Pearl et al. discloses an apparatus and method for stimulating hair growth. The Pearl et al. hand held laser provides distributed laser light to the scalp while simultaneously parting the user's hair to ensure that the laser light contacts the user's scalp. However, the rows of teeth have ends, which may scrap the scalp of a user, if the teeth make contact with the scalp of the user.

Accordingly, there is a clearly felt need in the art for a hand held laser device for stimulating hair growth, which may be moved on the scalp during a treatment without the risk of scraping the scalp.

SUMMARY OF THE INVENTION

The present invention provides a hand held laser device for stimulating hair growth. The hand held laser device for stimulating hair growth (laser device) includes a laser device body and at least one laser unit. Preferably, at least one light emitting diode (LED) is also included. The laser device body includes a skirt and a cover. The cover is attached to a top of the skirt. The skirt includes a contact skirt and a mounting plate. The contact skirt extends outward from substantially a perimeter of the mounting plate. At least one laser opening and preferably at least one LED opening is formed through the mounting plate. The at least one laser opening and the at least one LED opening is sized to receive the at least one laser unit and the at least one LED, respectively. An exterior surface of the cover is shaped to fit into the palm of a hand. A DC power supply is preferably used to power the at least one laser unit and the at least one LED. An electrical jack extends through a side wall of the cover. Preferably, an electrical switch is included to control power to the at least one laser unit and the at least one LED.

A plurality of round projections are formed on a bottom of the contact skirt. The plurality of round projections contact the scalp during a treatment with the laser device. A strap is preferably included, such that the laser device may be retained by a hand of a user. The strap includes a first strap portion and a second strap portion. One end of the first strap portion is secured to one side of the body and the other end of the first strap portion includes a first fastener portion. One end of the second strap portion is secured to an opposing side of the body and the other end of the second strap portion includes a second fastener portion. The first fastener portion engages the second fastener portion.

Accordingly, it is an object of the present invention to provide a laser device, which may be moved on the scalp during a treatment without the risk of scraping the scalp.

These and additional objects, advantages, features and benefits of the present invention will become apparent from the following specification.

DETAILED DESCRIPTION OF THE PREFERRED EMBODIMENTS

Figure 1:
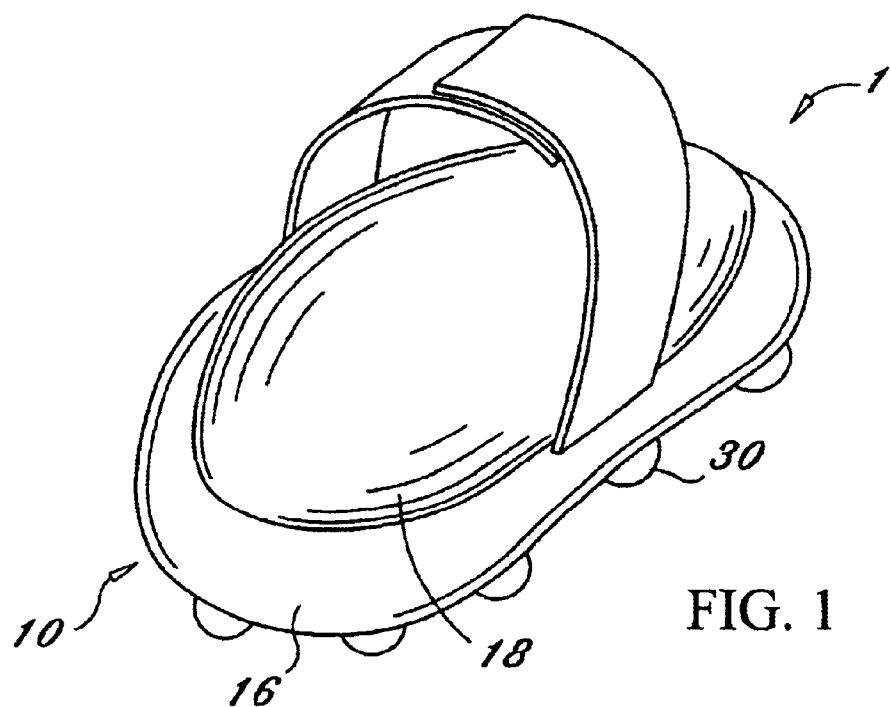
FIG. 1 is a perspective view of a laser device in accordance with the present invention.
Figure 2:
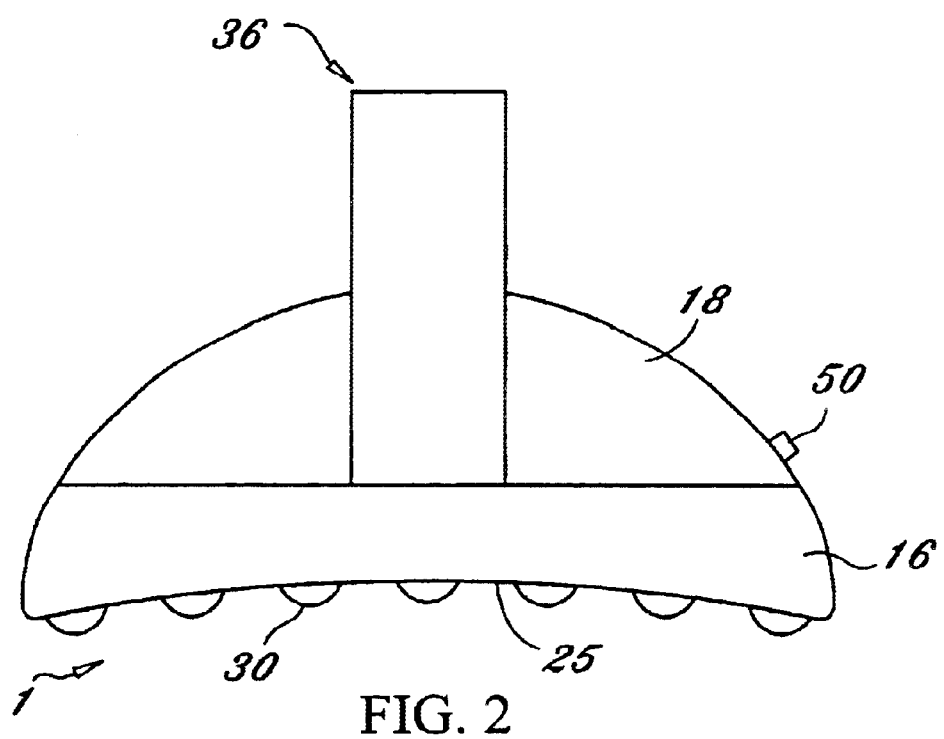
FIG. 2 is a side view of a laser device in accordance with the present invention.
Figure 3:
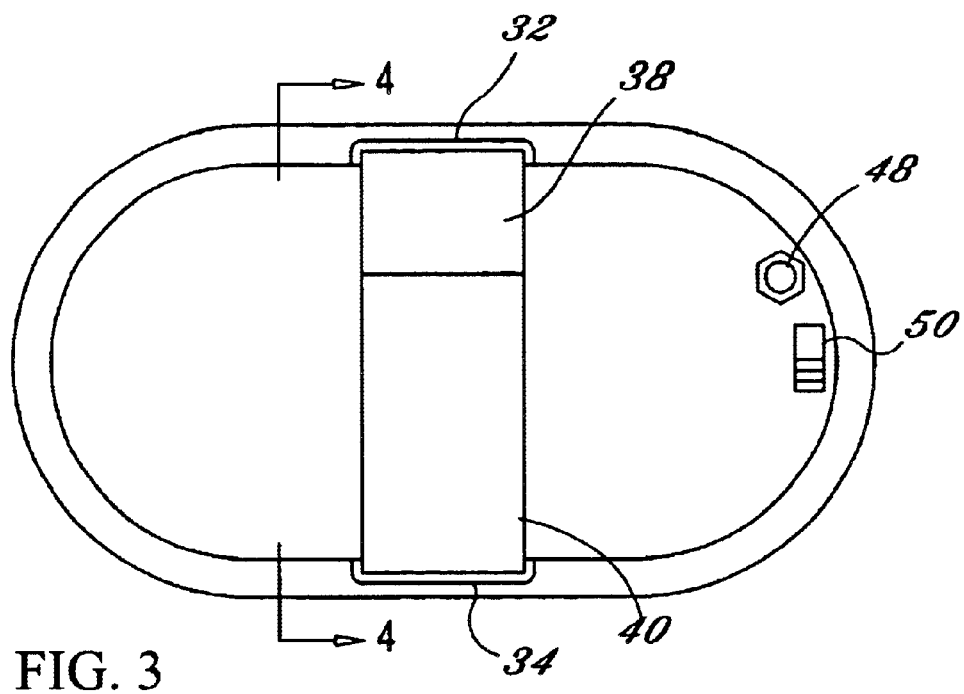
FIG. 3 is a top view of a laser device in accordance with the present invention.
Figure 4:
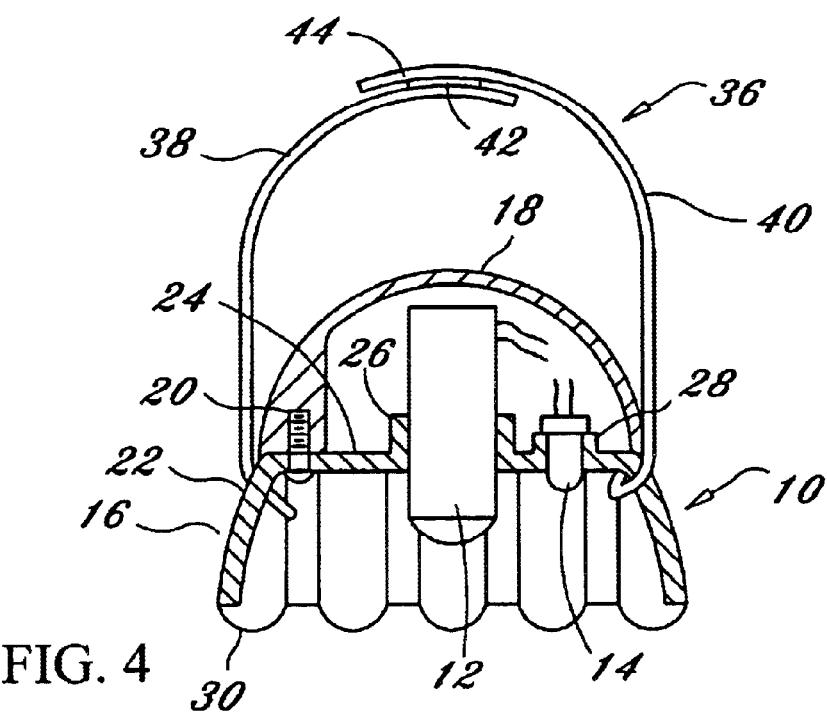
FIG. 4 is a cross sectional view of a laser device in accordance with the present invention.
Figure 5:
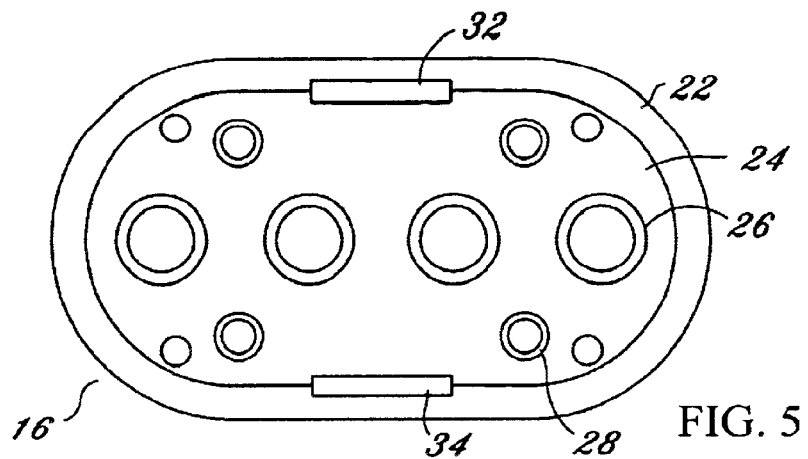
FIG. 5 is a top view of a laser device with a cover removed therefrom in accordance with the present invention.
Figure 6:
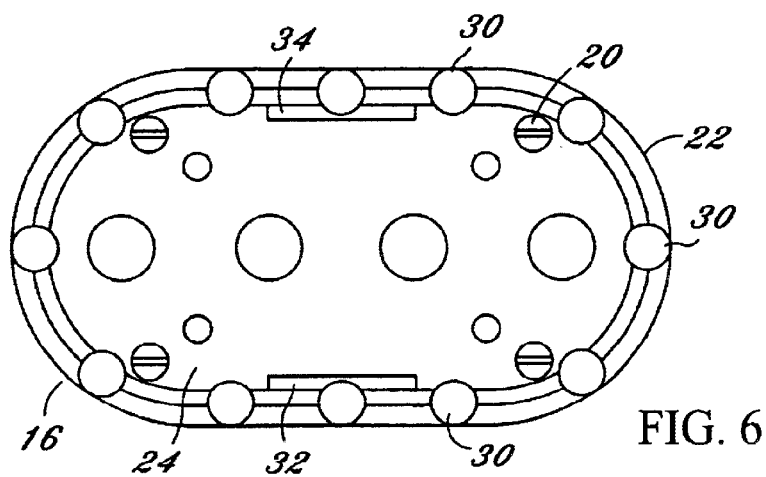
FIG. 6 is a bottom view of a laser device without a strap in accordance with the present invention.

With reference now to the drawings, and particularly to FIG. 1, there is shown a perspective view of a laser device 1. With reference to FIGS. 2–6, the laser device 1 includes a laser device body 10 and at least one laser unit 12. Preferably, at least one light emitting diode (LED) 14 is also included to provide extra light, to treat the scalp, besides the at least one laser unit 12. The laser device body 10 includes a skirt 16 and a cover 18. The cover 18 is preferably attached to a top of the skirt 16 with screws 20, but other attachment methods may also be used. An exterior surface of the cover 18 is shaped to fit into the palm of a hand. The skirt 16 includes a contact skirt 22 and a mounting plate 24. The contact skirt 22 extends outward from substantially a perimeter of the mounting plate 24. A curvature 25 is preferably formed on a bottom of each side of the contact skirt 22 to generally match the curvature of the scalp. Preferably, at least one laser boss 26 is formed in the mounting plate 24 to retain the at least one laser unit 12 and at least one diode boss 28 to retain the at least one LED 14. The at least one laser unit 12 is preferably retained in the at least one laser boss 26 with adhesive or any other suitable attachment method. The at least one LED 14 is preferably retained in the at least one LED boss 28 with adhesive or any other suitable attachment method.

A plurality of round projections 30 are formed on a bottom of the contact skirt 22. The width of each round projection 30 preferably exceeds the thickness of the contact skirt 22. The plurality of round projections 30 contact the scalp during a treatment with the laser device 1. A first strap slot 32 is formed through the skirt 16 at substantially the junction of the contact skirt 22 and the mounting plate 24 on one side thereof. A second strap slot 34 is formed through the skirt 16 at substantially the junction of the contact skirt 22 and the mounting plate 24 on the other side thereof. A strap 36 is preferably used to retain a hand in contact with the cover 18.

The strap 36 includes a first strap portion 38 and a second strap portion 40. One end of the first strap portion 36 is inserted through the first strap slot 32 and retained therein with any suitable method. A first fastener portion 42 is formed on the other end of the first strap portion 38. One end of the second strap portion 40 is inserted through the second strap slot 34 and retained therein with any suitable method. A second fastener portion 44 is formed on the other end of the second strap portion 40. The first fastener portion 42 engages the second fastener portion 44 to retain the other end of the first strap portion 38 relative to the other end of the second strap portion 40. The first and second fastener portions are preferably hook and loop fasteners, commonly sold under the trade name VELCRO. Other types of fastener portions may also be used.

Figure 7:
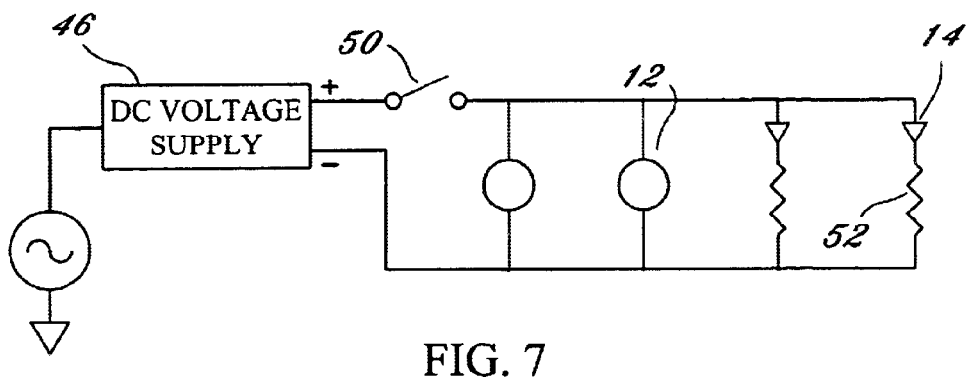
FIG. 7 is an electrical schematic of the laser device in accordance with the present invention.

With reference to FIG. 7, a DC power supply 46 is preferably used to power the at least one laser unit 12 and the at least one LED 14. The DC power supply 46 preferably receives power from a wall outlet. However, at least one battery may be substituted for the DC power supply 46. An electrical jack 48 is retained in the cover 18 to receive an input pin of the DC power supply 46. Preferably, an on-off switch 50 is connected between the DC power supply 46 and the at least one laser unit 12 and the at least one LED 14. The on-off switch 50 is retained in the cover 18. A slider on-off switch is preferably used, but other types of on-off switches may also be used. A voltage drop resistor 52 is preferably connected in series with each LED 14 to equal the voltage drop cross the at least one laser unit 12.

In use, an operator secures one hand to the cover 18 with the other hand by attaching the first strap portion to the second strap portion. The DC power supply is plugged into a wall outlet or the like. The input pin of the DC power supply is inserted into the electrical jack 48. The laser device 1 is placed on the scalp, such that the plurality of round projections 30 contact the scalp. The on-off switch 50 is closed to allow current to travel from the DC power supply 46 to the at least one laser unit 12 and the at least one LED 14. The laser device 1 is then moved over the scalp, until thereof has been fully treated.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A hand held laser device for stimulating hair growth on a scalp, comprising:

a laser device body including a skirt disposed on a bottom thereof;

at least one laser emitting device being retained in said laser device body, said at least one said laser emitting device being supplied with electrical power; and a plurality of projections being formed on a bottom of said skirt, wherein a bottom of at least two of said plurality of projections being in contact with the scalp when said hand held laser device is moved across the scalp during a treatment.

2. The hand held laser device for stimulating hair growth on a scalp of claim 1, further comprising:

said at least one laser emitting device being at least one LED.

3. The hand held laser device for stimulating hair growth on a scalp of claim 1, further comprising:

said at least one laser emitting device being at least one laser unit.

4. The hand held laser device for stimulating hair growth on a scalp of claim 1 wherein:

a curvature being formed on a bottom of each side of said skirt, said curvature generally matching the curvature of the scalp.

5. The hand held laser device for stimulating hair growth on a scalp of claim 1 further comprising:

said laser device body including a cover disposed on a top of said skirt.

6. The hand held laser device for stimulating hair growth on a scalp of claim 5 wherein:

an exterior surface of said cover being formed to fit into the palm of a hand.

7. The hand held laser device for stimulating hair growth on a scalp of claim 1, further comprising:

a strap being secured to said laser device body.

8. The hand held laser device for stimulating hair growth on a scalp of claim 1 wherein:

said bottom of each one of said plurality of projections being rounded.

9. A hand held laser device for stimulating hair growth on a scalp, comprising:

a laser device body including a skirt disposed on a bottom thereof, a curvature being formed on a bottom of each side of said skirt, said curvature generally matching the curvature of the scalp;

at least one laser emitting device being retained in said laser device body, said at least one laser emitting device being supplied with electrical power; and a plurality of projections being formed on a bottom of said skirt, a bottom of each one of said plurality of projections being rounded, wherein said bottom of at least two of said plurality of projections being in contact with the scalp when said hand held laser device is moved across the scalp during a treatment.

10. The hand held laser device for stimulating hair growth on a scalp of claim 9, further comprising:

said at least one laser emitting device being at least one LED.

11. The hand held laser device for stimulating hair growth on a scalp of claim 9, further comprising:

said at least one laser emitting device being at least one laser unit.

12. The hand held laser device for stimulating hair growth on a scalp of claim 9, further comprising:

said laser device body having a cover disposed on a top of said skirt.

13. The hand held laser device for stimulating hair growth on a scalp of claim 12 wherein:

an exterior surface of said cover being formed to fit into the palm of a hand.

14. The hand held laser device for stimulating hair growth on a scalp of claim 9, further comprising:

a strap being secured to said laser device body.

15. A hand held laser device for stimulating hair growth on a scalp, comprising:

a laser device body including a cover disposed on a top of a skirt, an exterior surface of said cover being formed to fit into the palm of a hand, a strap being secured to said laser device body for retaining a hand, a curvature being formed on a bottom of each side of said skirt, said curvature generally matching the curvature of the scalp;

at least one laser emitting device being retained in said laser device body, said at least one laser emitting device being supplied with electrical power; and a plurality of projections being formed on a bottom of said skirt, a bottom of each one of said plurality of projections being rounded, wherein said bottom of at least two of said plurality of projections being in contact with the scalp when said hand held laser device is moved across the scalp during a treatment.

16. The hand held laser device for stimulating hair growth on a scalp of claim 15, further comprising:

said at least one laser emitting device being at least one LED.

17. The hand held laser device for stimulating hair growth on a scalp of claim 15, further comprising:

said at least one laser emitting device being at least one laser unit.

* * * * *